United States Patent [19]
Graham et al.

[11] Patent Number: 5,859,342
[45] Date of Patent: Jan. 12, 1999

[54] ANTISENSE NUCLEOTIDE SEQUENCES AFFECTING FATTY ACID CATABOLISM IN PLANTS

[75] Inventors: Ian Alexander Graham; Mark Allen Hooks, both of Glasgow, United Kingdom

[73] Assignee: The University Court of The University of Glasgow, Glasgow, United Kingdom

[21] Appl. No.: 651,163

[22] Filed: May 17, 1996

[51] Int. Cl.$^6$ .............................. A01H 4/00; C12N 5/04; C12N 15/00; C07H 21/00

[52] U.S. Cl. ..................... 800/205; 800/250; 536/24.5; 435/410; 435/419; 435/320.1; 435/252.1

[58] Field of Search ....................... 800/250, 205; 536/24.5; 435/410, 419, 320.1, 252.1

[56] References Cited

U.S. PATENT DOCUMENTS 5,107,065  4/1992  Shewmaker .............................. 800/205
5,498,544  3/1996  Gengenbach et al. ................. 435/320.1

OTHER PUBLICATIONS

Hooks et al. Plant Physiology, vol. 105, No. 1, suppl. May 1994, p. 131, Abstract No. 710.

Kindl. Biochemie, vol. 75, 1993, pp. 225–230.

Newman et al. Plant Physiol. 1994, vol. 106 pp. 1241–1255, 1994.

V.S. Eccleston et al; Medium–chain fatty acid biosynthesis and utilization in *Brassica napus* plants expressing lauroy-1–acyl carrier protein thioesterase; *Planta* 198: 46–53 (1996).

T.A. Voelker et al; Genetic engineering of a quantitative trait: metabolic and genetic parameters influencing the accumulation of laurate in rapeseed; *the Platn Journal* 9: 229–241 (1996).

M.A. Hooks et al; Regulation of Acyl–CoA Oxidases in Maize Seedlings; *Phytochemistry* 40:657–660 (1995).

M.A. Hooks, M.B. Ahmed, I.A. Graham; An Investigation of Fatty Acid β–Oxidation in *Arabidopsis Thaliana*; Poster Presentation at: 1995 Biochemistry and Molecules Biology of Plant Fatty Acids and Glycerolipids Symposium, South Lake Tahoe, CA, USA, Jun. 1–4, 1995.

*Primary Examiner*—Ponnathapura Achutamurthy
*Assistant Examiner*—Phuong T. Bui
*Attorney, Agent, or Firm*—Bell Seltzer Intellectual Law Property of Alston & Bird, LLP

[57] ABSTRACT

Nucleotide sequences encoding antisense RNA to proteins having enzymic activity in β-oxidation, constructs, vectors, plants and plant cells comprising such nucleotide sequences, and uses of such nucleotide sequences.

13 Claims, 12 Drawing Sheets

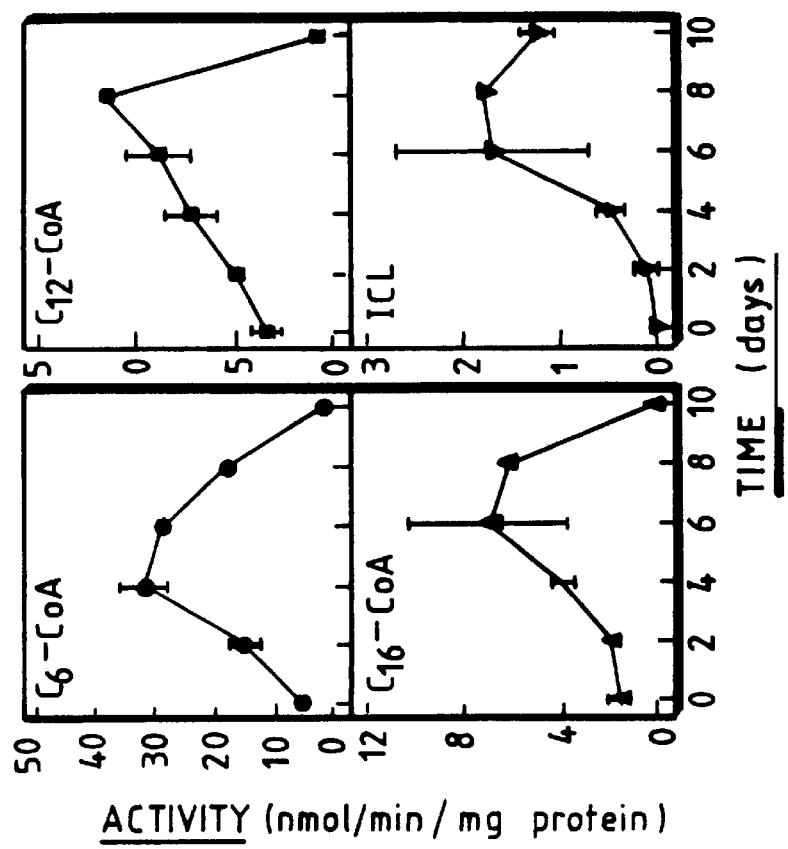
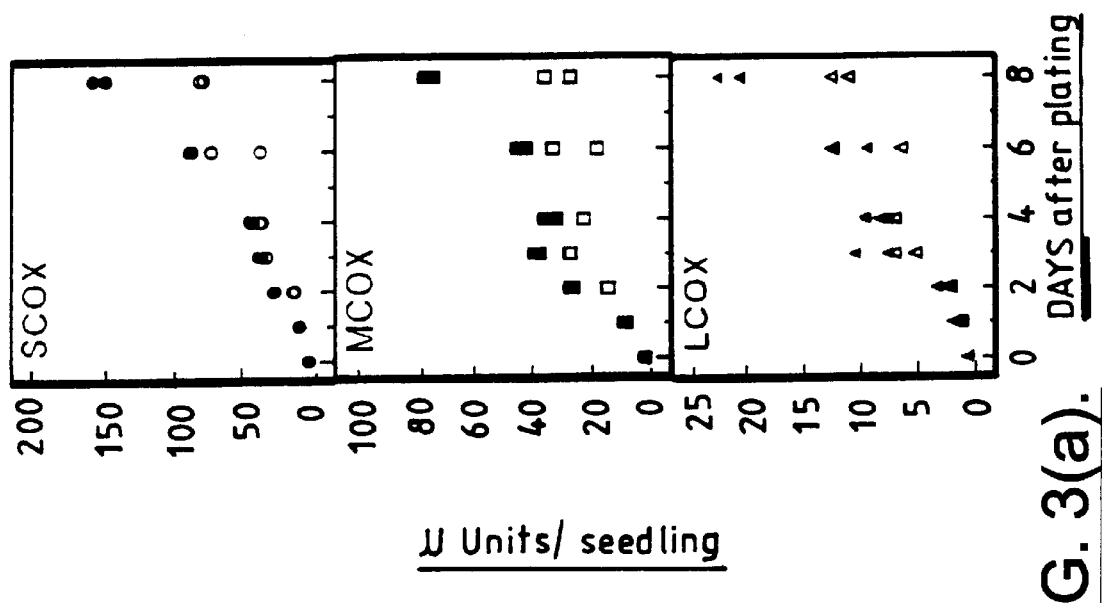
FIG. 3(b).
FIG. 3(a).

cDNA = 5F, 35H, or 39H
OCS — Octopine Synthase Terminator
pNOS — Nopaline Synthase Promoter
HPT II — gene conferring resistance to Hygromycin
PS-5' & PS-3' — Primer sites OCS — Octopine synthase terminator
pNOS — Nopaline synthase promoter
HPT II — gene conferring resistance to Hygromycin
PS-5' & PS-3' — Primer sites

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
  ( A ) LENGTH: 400 base pairs
  ( B ) TYPE: nucleic acid
  ( C ) STRANDEDNESS: double
  ( D ) TOPOLOGY: linear ( i i ) MOLECULE TYPE: cDNA ( v i ) ORIGINAL SOURCE:
  ( A ) ORGANISM: Arabidopsis thaliana ( v i i ) IMMEDIATE SOURCE:
  ( B ) CLONE: 35H7T7

( x i ) SEQUENCE DESCRIPTION: SEQ ID NO:1:

```
ATTGAGACAC  AGGTGATTGA  TTATAAAACT  CAGCAGAACA  GGCTATTTCC  TCTGCTAGCA    60
TCTGCATATG  CATTTCGATT  TGTTGGAGAG  TGGCTAAAAT  GGCTGTACAC  GGATGTAACT   120
GAAAGACTGG  CGGCTAGTGA  TTTCGCAACT  TTGCCTGAGG  CTCATGCATG  CACTGCAGGA   180
TTGAAGTCTC  TCACCACCAC  AGCCACTGCG  GATGGCATTG  AAGAATGTCG  TAAGTTATGT   240
GGTGGACATG  GATACTTGTG  GTGCAGTGGG  CTCCCCGAGC  TGTTTGCTGT  ATATGTTCCT   300
GCCTGCACAT  ACGAAGGAGA  CAATGTTGTG  CTGCAATTAC  AGGTTGCTCG  ATTCCTCATG   360
AAGACAGTCG  CCCAGCTGGG  ATCTNGAAAG  GTTCNGTTTG                           400
```

( 2 ) INFORMATION FOR SEQ ID NO:2:

( i ) SEQUENCE CHARACTERISTICS:
  ( A ) LENGTH: 470 base pairs
  ( B ) TYPE: nucleic acid
  ( C ) STRANDEDNESS: double
  ( D ) TOPOLOGY: linear ( i i ) MOLECULE TYPE: cDNA ( v i ) ORIGINAL SOURCE:
  ( A ) ORGANISM: Arabidopsis thaliana ( v i i ) IMMEDIATE SOURCE:
  ( B ) CLONE: 5F12T7P ( x i ) SEQUENCE DESCRIPTION: SEQ ID NO:2:

```
GTGCGTTGAG  ATTCCGTTCT  GTGAGAATAC  CCCGTGATAA  TCTTCTCAAT  CGTTTTGGAG    60
ATGTGTCCCG  AGATGGGACG  TATACAAGTA  GTTTGCCAAC  AATCAATAAA  AGATTTGGTG   120
CAACACTCGG  TGAGCTTGTA  GGTGGTCGAG  TTGGCCTTGC  CTATGCATCT  GTTGGCGTCC   180
```

```
TTAAAATCTC  TGCAACGATT  GCCATTCGTT  ATTCTCTTCT  AAGACAACAA  TTCGGGCCTC      240

CAAAGCAACC  TGAGGTCAGT  ATTCTCGATT  ACCAGTCTCA  ACAACACAAG  CTCATGCCGA      300

TGTTAGCCTC  CACCTATGCA  TACCATTTTG  CAACTGTATA  CCTTGTGGGG  GAATATTCAG      360

AGATGAAGAA  GGCTCACGGT  GAGCAATTGG  TTGCTGATGT  CCATGCACTC  TCTGCTGGGC      420

TCAAATCTTT  GTACGGGTTT  CACGCAGGGT  CTCGCCTTAG  AAAGCTTTG                   470
```

( 2 ) INFORMATION FOR SEQ ID NO:3:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Arabidopsis thaliana ( v i i ) IMMEDIATE SOURCE:
        ( B ) CLONE: FAFJO1

( x i ) SEQUENCE DESCRIPTION: SEQ ID NO:3:

```
CCTGGTGGGA  AGCCTATATC  AGTACCTGAT  AAAGAAATTG  TAGAGATGAT  CTTATTCCCT       60

GTTGTCAACG  AGGCATGCCG  CGTCCTAGAT  GAAGGAGTTG  TGATCCGAGC  CTCAGACTTG      120

GACATTGCGT  CTGTCCTTGG  AATGAGTTTT  CCTTCTTACC  GGGGAGGAAT  TGTTTTCTGG      180

GCAGACACTG  TTGGCCCAAA  GTACATATAT  GAGAGGCTCA  AGAAATTGTC  GGAGACTTAT      240

GGCAGCTTTT  TCAMACCATC  GAGGTATCTG  GAGGAAAGAG  CAATGCAATG  GAATGCTTTT      300

TGAGTGAATC  GAAATCGTCG  AGGTCCACAT  TGTGACGGCG  TTTCA                      345
```

( 2 ) INFORMATION FOR SEQ ID NO:4:

( i ) SEQUENCE CHARACTERISTICS:
        ( A ) LENGTH: 400 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Arabidopsis thaliana ( v i i ) IMMEDIATE SOURCE:
        ( B ) CLONE: 39H3T7

( x i ) SEQUENCE DESCRIPTION: SEQ ID NO:4:

```
AACAGATCCG  AATTTTATCT  TTAATCAGCC  GGAAAAAATG  GAGAAAGCGA  TCGAGAGACA       60

ACGNGTTCTT  CTTGAGCATC  TCCGACCTTC  TTCTTCTTCT  TCGCACAATT  ACGAGGCTTC      120

TCTATCTGCT  TCTGCTTGCT  TGGCTGGGGA  CAGTGCTGCA  TATCAGAGGA  CCTCTCTCTA      180

TGGAGATGAT  GTTGTCATTG  TCGCGGCACA  TAGGNCTCCA  CTATGCAAGT  CCAAACGTGG      240

CAATTTCAAG  GGTACATATC  CCGCTGATTT  GCTCGCACCT  NTTTTGAGGG  CATTGATAGA      300

GAAGACGCAT  CTAAACCCCC  NGTGAAGTAG  GTGACATTTT  TGTGGGNACT  CTTTTTGCAC      360

CNCGNTCTTA  GAGAGGCCAC  TTGANTTCAG  GNATGGCTGC                              400
```

ANTISENSE NUCLEOTIDE SEQUENCES AFFECTING FATTY ACID CATABOLISM IN PLANTS

FIELD OF INVENTION

The present invention relates to cells exhibiting a lower rate of the β-oxidation of fatty acids, processes for obtaining such cells, and genetic material therefor. In particular, the cells are plant cells.

BACKGROUND OF THE INVENTION

Crop plants, such as oilseed rape, sunflower and corn, are valuable agronomically as sources of oils which can be used for many purposes ranging from use as industrial feed stocks to use in margarine manufacture and even as potential alternatives to fossil fuels.

The production of naturally occurring oils in oil producing plants has been augmented hitherto using conventional breeding techniques. Generally speaking, it is the seeds of oil producing plants which are harvested and then processed for their oil content, the rest of the plant generally being left as waste.

Recently, it has been proved that recombinant DNA technology can be used, for example, on oil seed rape to produce fatty acids which are not found naturally in the non-transformed plant. Voelker et al. Plant Journal (1996) 9: 229–241 succeeded in engineering lauric acid production into oil seed rape. Lauric acid is a fatty acid not normally found in any significant quantity in oil seed rape. Although, the production of lauric acid in oil seed rape was achieved, it has been found that the presence of lauric acid also plays a part in activating fatty acid catabolism (β-oxidation pathway), thus creating a so-called "futile cycle" wherein lauric acid is produced which in turn plays a role in initiating its own catabolism, begin degraded and resulting in decreased yields of lauric acid in such plants (Eccleston V. S. et al., *Planta* (1996) 198:46–53).

There exists a need to improve the overall yield of fatty acids and/or lipids in oil seed bearing plants. For the purposes of the description oil bearing plants are to be construed as plants which are agronomically attractive for their fatty acid and/or lipid generating potential and/or capacity. In particular, there exists a need to modify the β-oxidation pathway in plants, thereby improving overall yield of naturally occurring fatty acids or non-naturally occurring fatty acids (i.e., fatty acid production as a result of recombinant DNA manipulation) in oil seed bearing plants.

SUMMARY OF THE INVENTION

An object of the present invention is to provide plants, in particular oil seed bearing plants with improved yields of oils in the seeds.

A second object of the invention is to improve fatty acid and/or lipid levels in plant tissues other than seeds.

These and other object of the invention will become apparent from the following description and examples.

BRIEF DESCRIPTION OF THE FIGURES

FIG. 3A shows the ACOX activity in Arabidopsis seedlings grown with (solid symbols) and without (open symbols) sucrose.

FIG. 3B shows the ACOX activity in Arabidopsis sensescing leaves.

DETAILED DESCRIPTION OF THE INVENTION

Figure 1:
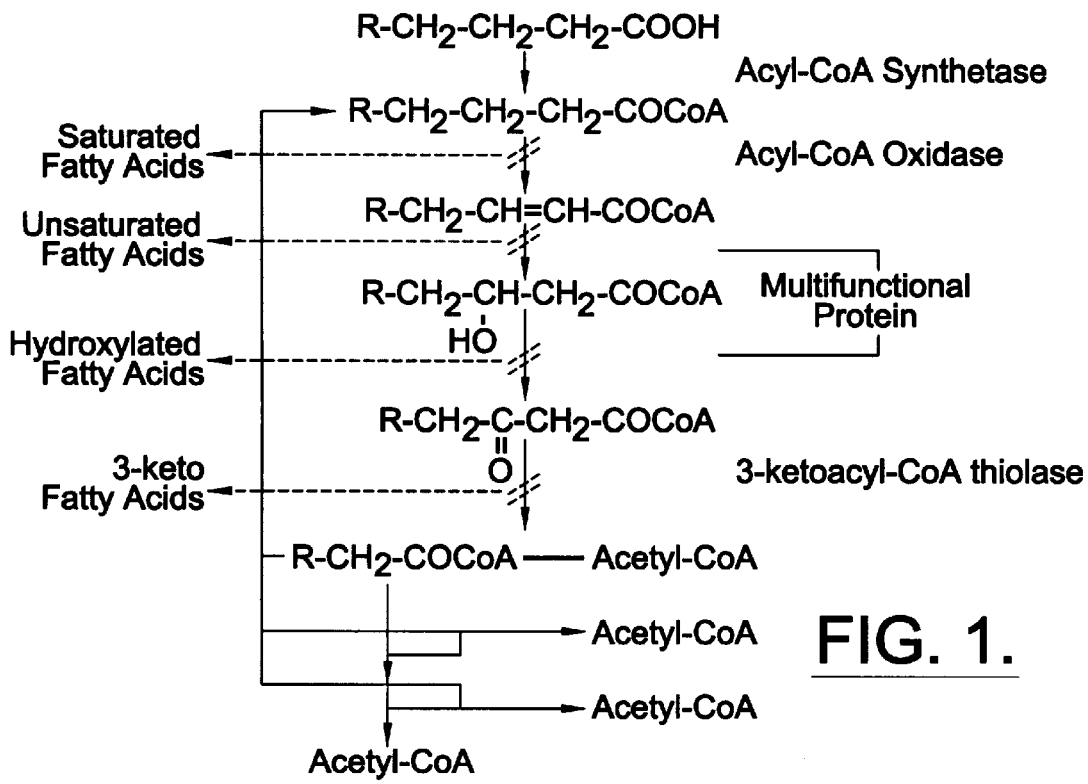
FIG. 1 shows the pathway of β-oxidation, showing end-products formed with a reduced or missing enzymatic activity (broken lines and arrows).

According to the present invention there is provided a nucleotide sequence encoding an antisense RNA molecule complementary to a sense mRNA molecule encoding for a protein having an enzymic activity in β-oxidation of fatty acids in a plant, which nucleotide sequence is under transcriptional control of a promoter and a terminator, both promoter and terminator capable of functioning in plant cells.

The nucleotide sequence encoding the antisense RNA molecule can be of any length provide that the antisense RNA molecule transcribable therefrom is sufficiently long so as to be able to form a complex with a sense mRNA molecule encoding for a protein having an enzymic activity in the β-oxidation pathway. Thus, without the intention of being bound by theory it is thought that the antisense RNA molecule complexes with the mRNA of the protein and prevents or substantially inhibits the synthesis of functional protein(s) having enzymic activity in the β-oxidation pathway. As a consequence of the interference of the antisense RNA enzyme activity of protein(s) involved in the β-oxidation of fatty acids is decreased.

For the purposes of the description "nucleotide sequence" will be referred to as DNA unless there is different indication. The DNA encoding the antisense RNA can be from about 50 nucleotides in length up to the length of the relevant mRNA produced by the cell. Preferably, the length of the DNA encoding the antisense RNA will be from 100 to 1500 nucleotides in length. The preferred source of antisense RNA for DNA constructs of the present invention is DNA showing substantial identity or similarity to the genes or fragments thereof of proteins having enzymic activity involved in the three major steps of β-oxidation in plants. Thus the encoding DNA of constructs of the present invention may be selected from the group acyl-CoA oxidases, for example long chain acyl CoA ($C_{16}$-CoA), medium chain acyl CoA ($C_{12}$-CoA) and/or short chain acyl CoA ($C_6$-CoA) oxidases (Hooks et al. (1995) Phytochemistry 40, p. 657), multi-functional protein and 3-ketoacyl-CoA thiolase or fragments thereof such as enzymically active fragments thereof.

The promoter is a nucleotide sequence upstream from the transcriptional initiation site and which contains all the regulatory regions required for transcription. Examples of promoters suitable for use in DNA constructs of the present invention include viral, fungal, bacterial, animal and plant derived promoters capable of functioning in plant cells. The promoter may be selected from so-called constitutive promoters or inducible promoters. Examples of suitable inducible or developmentally regulated promoters include the napin storage protein gene (induced during seed development), the malate synthase gene (induced during seedling germination), the small sub-unit RUBISCO gene (induced in photosynthetic tissue in response to light), the patatin gene highly expressed in potato tubers and the like. Alternatively, the promoter could be selected to express the DNA constitutively, that is, in all living tissues of the plant. It will be appreciated that the promoter employed should give rise to the transcription of a sufficient amount of the antisense RNA molecule at a rate sufficient to cause an inhibition of fatty acid catabolism in plant cells. The required amount of antisense RNA to be transcribed may vary from plant to plant. Examples of suitable promoters include the cauliflower mosaic virus 35S (CaMV 35S) and 19S (CaMV 19S) promoters, the nopaline synthase promoter, octopine synthase promoter, heat shock 80 (hsp 80) promoter and the like. Generally, in plants and plant cells of the invention inducible or developmentally regulated promoters are preferred.

A terminator is contemplated as a DNA sequence at the end of a transcriptional unit which signals termination of transcription. These elements are 3'-non-translated sequences containing polyadenylation signals which act to cause the addition of polyadenylate sequences to the 3' end of primary transcripts. Sequences mentioned above may be isolated from funghi, bacteria, animals or plants.

Examples of terminators particularly suitable for use in nucleotide sequences and DNA constructs of the invention include the nopaline synthase polyadenylation signal of *Agrobacterium tumefaciens,* the 35S polyadenylation signal of CaMV, octopine synthase polyadenylation signal and the zein polyadenylation signal from *Zea mays.*

The skilled addressee will appreciate that nucleotide sequences as defined herein may be introduced to plant cell genomes of oil bearing plants already transgenic for oils which do not occur naturally in native, non-transformed plants. An example of a plant of this type is *Brassica napus* which is transgenic for lauric acid production. Nucleotide sequences of the invention can be introduced into the plant cell genome of such plants. It is thought that such introduced antisense nucleotide sequences of the invention will reduce futile recycling of non-naturally occurring fatty acids produced in plants genetically transformed for the production thereof.

In a further aspect of the invention there is provided a nucleotide sequence (nucleotide sequence according to the invention) comprising a transcriptional regulatory sequence, a sequence under the transcriptional control thereof which encodes an RNA which consists of a plurality of subsequences, characterized in that the RNA subsequences are antisense RNAs to mRNAs of proteins having an enzymic activity in the peroxisomal β-oxidation of fatty acids in plant cells.

The nucleotide sequence may encode an RNA having any number of subsequences. Preferably, the number of subsequences lies between 2 and 7 (inclusive) and more preferably lies between 2 and 4.

In one preferment, the RNA encoded by the contiguous sequence comprises a cleavage site, such as a ribozyme or restriction enzyme site such as XbaI, SalI, KpnI or the like, between two of the subsequences so that the RNA can be cleaved into regions comprising said subsequences, or even into the subsequences per se. Naturally, the skilled addressee will appreciate that the subsequences contained within the RNA encoded by the contiguous sequence resulting from such cleavage will not contain a 5' cap or a ribozome binding site and will thus not be translated when present in a eukaryotic cell, such as a plant cell.

The invention still further provides a nucleotide sequence which is similar to the above disclosed antisense RNA sequences. By "similar" is meant a test sequence which is capable of hybridising to a sequence which is complementary to the invention nucleotide sequence. When the test and inventive sequences are double stranded the nucleic acid constituting the test sequence preferably has a Tm within 20° C. of that of the inventive sequence. In the case that the test and inventive sequences are mixed together and denatured simultaneously, the Tm values of the sequences are preferably within 10° C. of each other. More preferably the hybridization is performed under stringent conditions, with either the test or inventive DNA preferably being supported. Thus either a denatured test or inventive sequence is preferably first bound to a support and hybridization is effected for a specified period of time at a temperature of between 50° and 70° C. in double strength SSC (2×NaCl 17.5 g/l and sodium citrate (SC) at 8.8 g/l)buffered saline containing 0.1% sodium dodecyl sulphate (SDS) followed by rinsing of the support at the same temperature but with a buffer having a reduced SSC concentration. Depending upon the degree of stringency required, and thus the degree of similarity of the sequences, such reduced concentration buffers are typically single strength SSC containing 0.1% SDS, half strength SSC containing 0.1% SDS and one tenth strength SSC containing 0.1% SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1% SDS.

The invention still further provides a nucleotide sequence which is complementary to one which hybridizes under stringent conditions with the above disclosed nucleotide sequences.

The invention also provides a DNA construct comprising the nucleotide sequence according to the invention, as well as a biological vector comprising the said sequence or construct. The biological vector may be a virus or bacterium, such as *Agrobacterium tumefaciens,* for example, and the construct advantageously further encodes a marker protein, such as one having herbicide resistance, or anti-bacterial properties.

DNA constructs and nucleotide sequences of the invention may be used to transform cells of both monocotyledonous and dicotyledonous plants in various ways known in the art. For example, particle bombardment of embryogenic callus is the method of choice for production of transgenic monocotyledonous plants [Vasil (1994) *Plant Mol. Biol.* 25, 925–937]. In many cases transformed plant cells may be cultured to regenerate whole plants which can subsequently reproduce to give successive generations of genetically modified plants.

The invention still further provides eukaryotic cells, such as plant cells (including protoplasts) for example, containing the said nucleotide sequence, DNA construct or vector.

The invention still further provides plants comprising such plant cells, the progeny of such plants which contain the sequence stably incorporated and hereditable in a Mendelian manner, and/or the seeds of such plants or such progeny. Such plants include field crops including sunflower, oilseed rape, soybean, castorbean, maize, olive, linseed and cuphea. Plants and/or plant cells of the Brassicaceae are particularly preferred, such as oilseed rape and Arabidopsis. By "modified fatty acid content" is meant a cell which exhibits non-wild type proportions of fatty acids and/or lipids due to under-expression of an enzymic protein of β-oxidation.

The invention still further provides the use of the sequence according to the invention, whether "naked" or present in a DNA construct or biological vector—in the production of eukaryotic cells, particularly plant cells having a modified fatty acid content.

The invention still further provides a method of inducing an under expression of an enzymic protein of β-oxidation in plant cells comprising introducing into such cells a nucleotide sequence according to the invention, or a construct or vector containing it.

The invention still further provides a method of inhibiting the production of at least one enzyme in a eukaryotic cell comprising introducing into the said cell a nucleotide sequence comprising a transcriptional regulatory sequence and a sequence contiguous therewith and under the transcriptional control thereof, which contiguous sequence encodes an RNA which consists of a single subsequence or a plurality of subsequences, characterized in that the subsequence or subsequences have the sequences of antisense RNA's to mRNA's of proteins having an enzymic activity in the peroxisomal β-oxidation of fatty acids in a plant.

Examples of the nucleotide sequences of the invention are provided below. These examples relate to the production of plants of the family Brassicaceae such as oil seed rape and Arabidopsis.

1. The nucleotide sequence of the invention may encode an mRNA which consists—in the 5' to 3' direction—of (i) a promoter, (ii) at least one cDNA in reverse orientation i.e. 3' to 5' orientation, (III) a terminator, (iv) optionally a further promoter, (v) the coding region of the HPT II gene (hygromycin) and (vi) optionally a further stop codon. When such a sequence is introduced into the cells of Brassicaceae plants, the sequence encoding the mRNA is transcribed. The region of the thus transcribed mRNA which encodes the HPT II gene is translated, whilst the region of the mRNA which encodes the cDNA is not.

2. The nucleotide sequence of the invention may encode an mRNA which consists—in the 5' to 3' direction—of (i) a promoter, (ii) the coding region of the HPT II gene, (iii) a translation stop codon, (iv) optionally a further start codon, (v) a region encoding at least one cDNA in reverse orientation i.e. 3' to 5' orientation and (vi) optionally a further stop codon. When such a sequence is introduced into the cells of Brassicaceae plants, the sequence encoding the mRNA is transcribed. The region of the thus transcribed mRNA which encodes the HPT II gene is translated, whilst the region of the mRNA which encodes the cDNA in reverse orientation i.e. 3' to 5' orientation is not translated.

3. The nucleotide sequence of the invention may encode an mRNA which comprises in the 5' to 3' direction (i) a promoter, (ii) a cDNA in reverse orientation i.e. 3' to 5' orientation, (iii) a terminator, (iv) a promoter, (v) the coding region of the HPT II gene (hygromycin), (vi) a terminator, (vii) a promoter, (viii) a second cDNA in reverse orientation i.e. 3' to 5' orientation, (ix) a terminator. When such a sequence is introduced into the cells of Brassicaceae plants, the sequences encoding (ii) and (viii) are transcribed. The region of the thus transcribed mRNA which encodes the HPT II gene is translated, whilst the regions of the mRNA encoding the cDNA is not.

Naturally the skilled addressee will also appreciate that the two (2) (or more) cDNA's in reverse orientation could be adjacent to one another and located upstream or downstream of a marker gene, if present.

The invention will now be described with reference to the following Figures and Examples which are not to be construed as limiting the invention.

FIG. 1: Pathway of β-oxidation showing end-products formed with a reduced or missing enzymatic activity (broken lines and arrows).

Figure 2B:
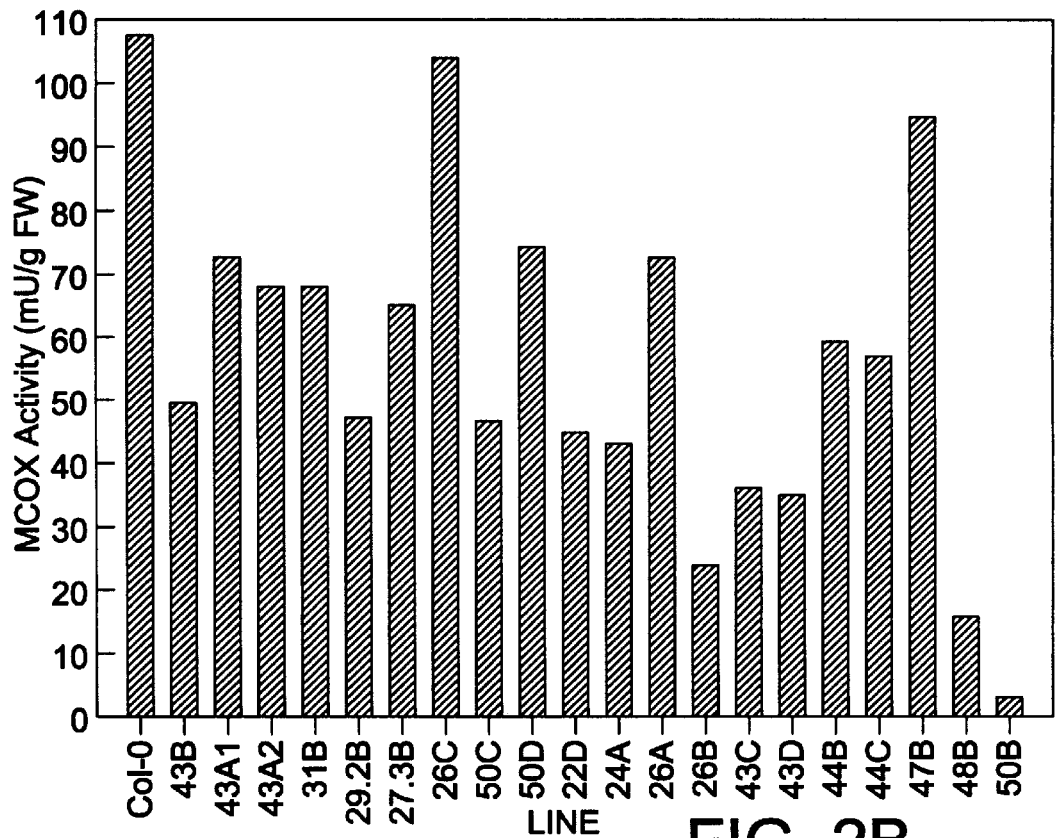
FIG. 2B shows the ACOX activity in Arabidopsis (EMS) mutants requiring exogenous carbohydrate for early post-germinative growth.
Figure 2A:
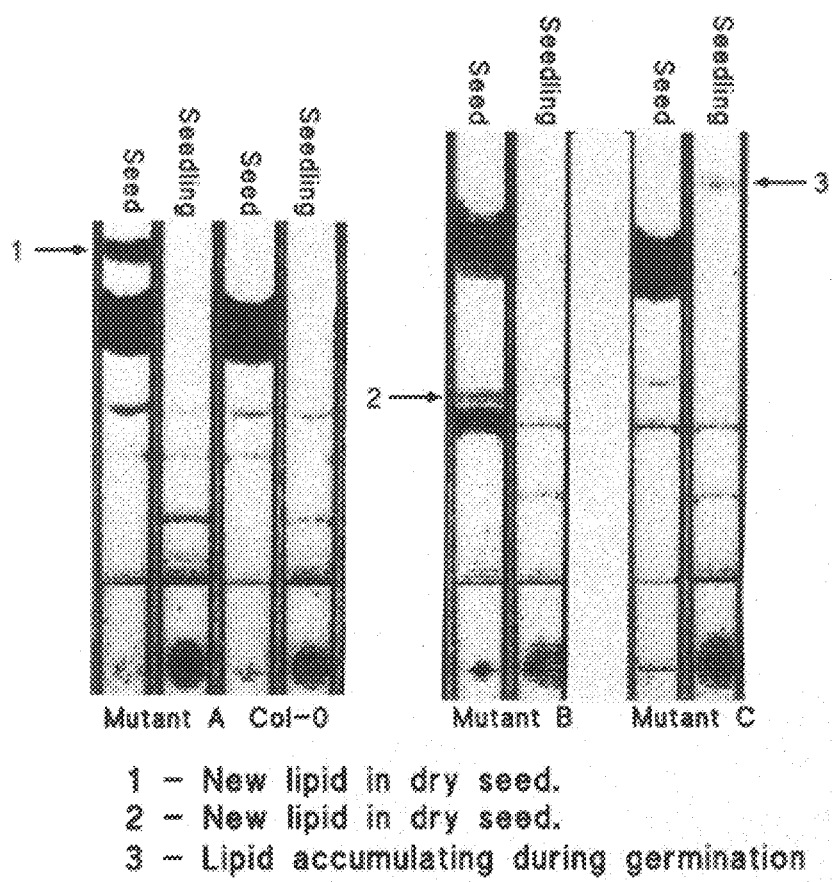
FIG. 2A shows the fatty acid activity in Arabidopsis (EMS) mutants requiring exogenous carbohydrate for early post-germinative growth.

FIG. 2A & 2B: Fatty acids and ACOX activities in Arabidopsis (EMS) mutants requiring exogenous carbohydrate for early post-germinative growth.

FIG. 3A & 3B: ACOX activity in Arabidopsis during two different developmental states.

Figure 4A:
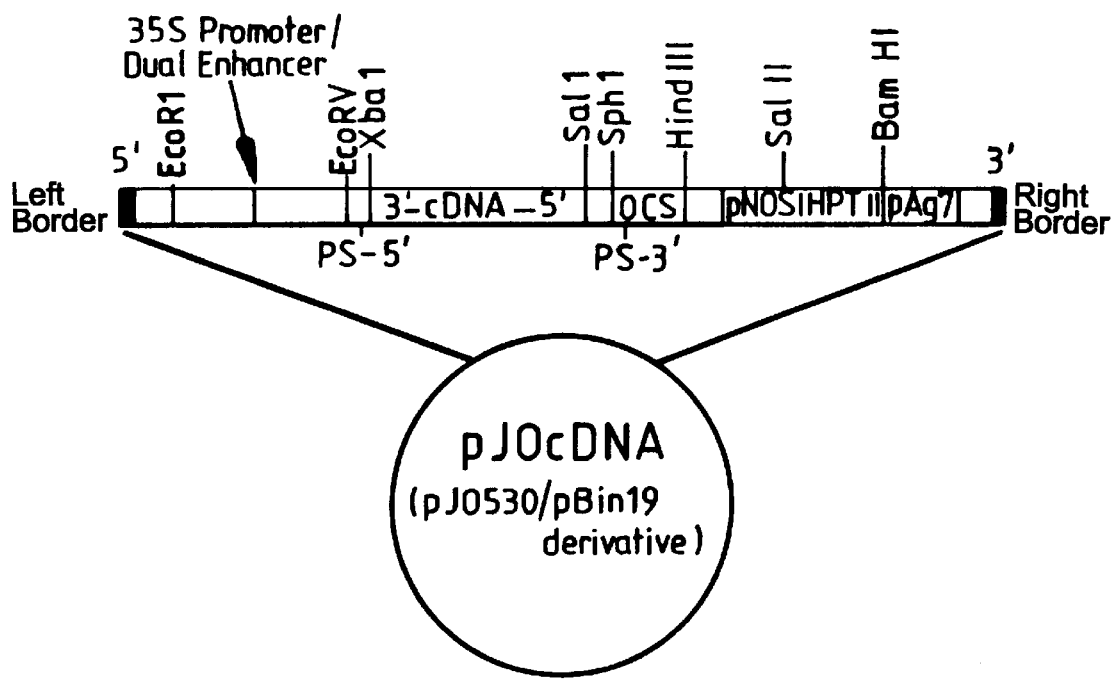
FIG. 4A is a generic map of plasmid vectors pJO5F, pJO35H, and pJO39H.
Figure 4B:
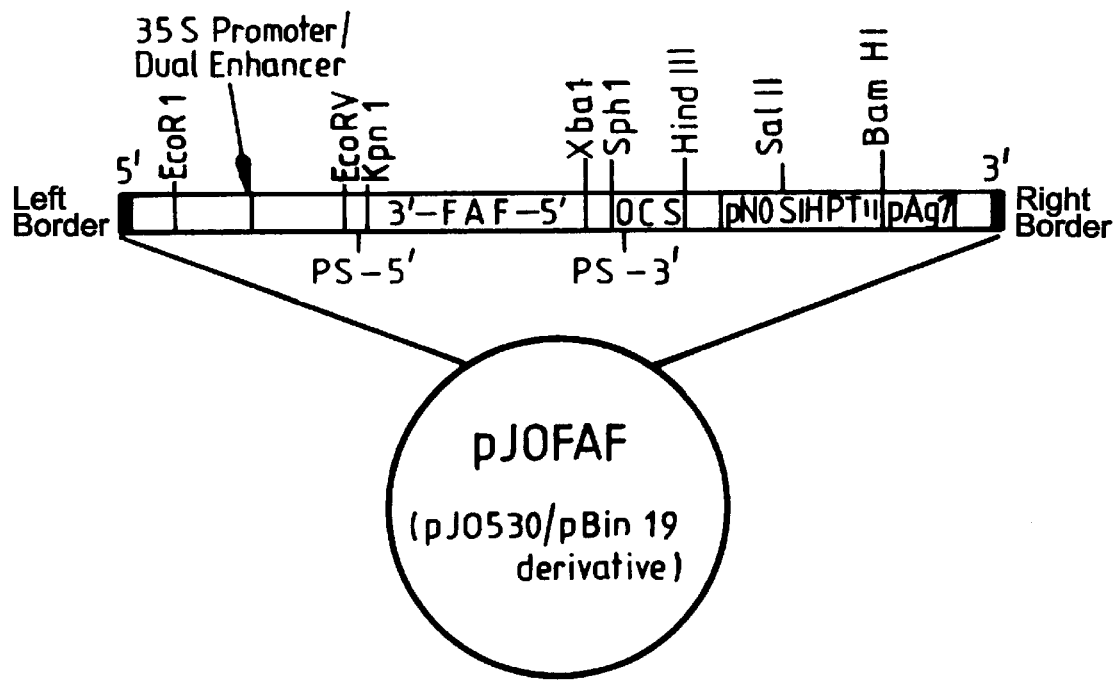
FIG. 4B is a generic map of plasmid vector pJOFAF.

FIG. 4A & 4B: Maps of transformation vectors.

Figure 5:
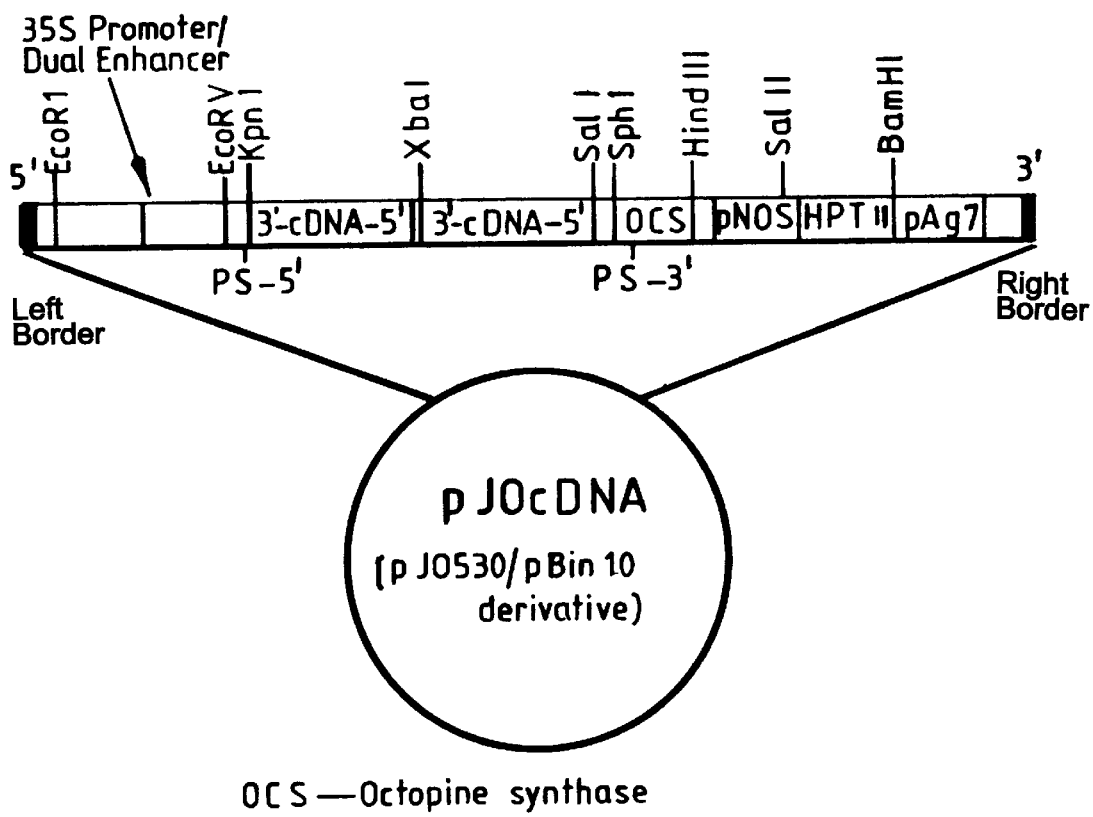
FIG. 5 is a generic map of a double antisense vector.

FIG. 5: Map of double antisense vector.

Figure 6A:
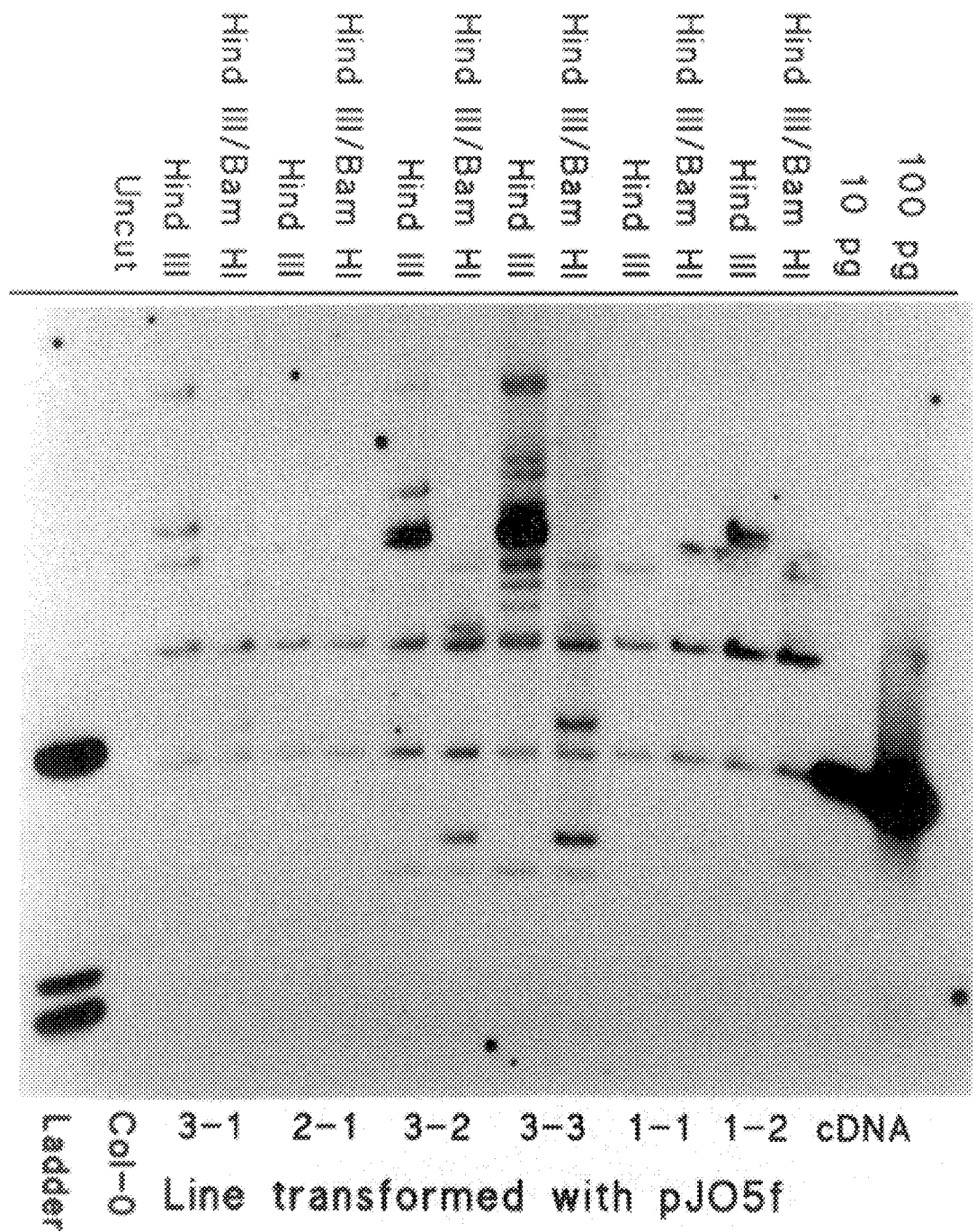
FIG. 6A is a Southern blot showing incorporation of cDNA into the genome of Arabidopsis transformed with pJO5F.
Figure 6B:
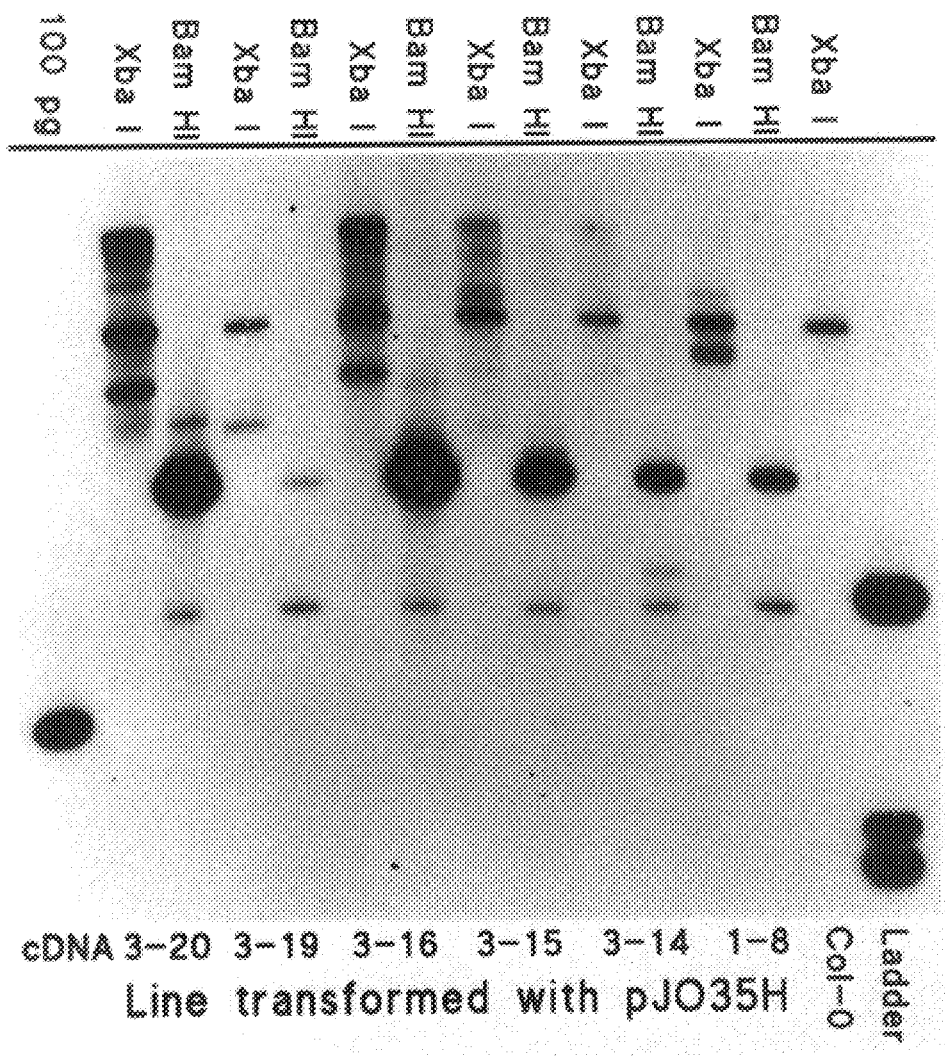
FIG. 6B is a Southern blot showing incorporation of cDNA into the genome of Arabidopsis transformed with pJO35H.

FIG. 6: Southern blots showing incorporation of cDNA into the genome of Arabidopsis.

Figure 7A:
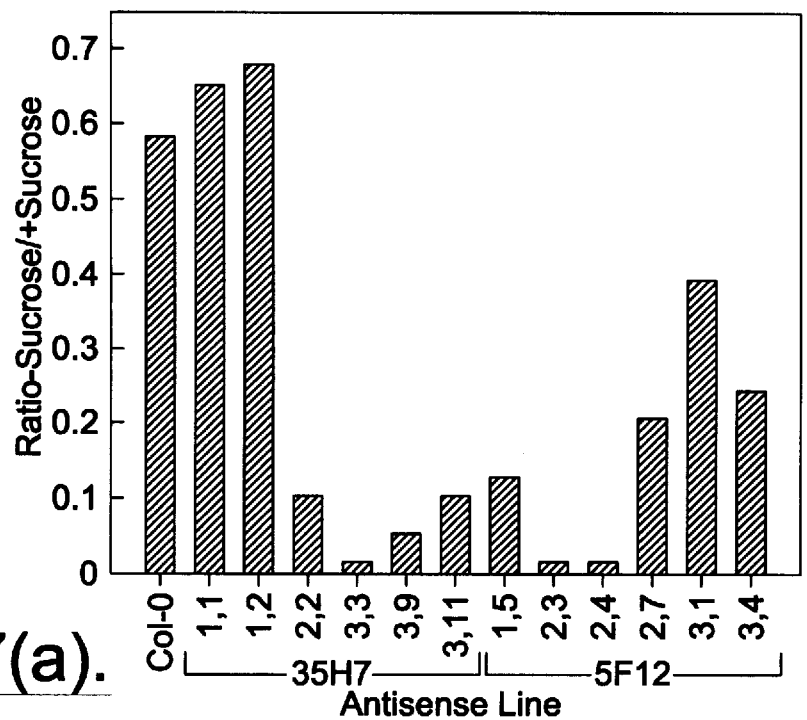
FIG. 7A is a graph showing the dependence of early post-germinative root growth of ACOX antisense seedlings on exogenous carbohydrates.
Figure 7B:
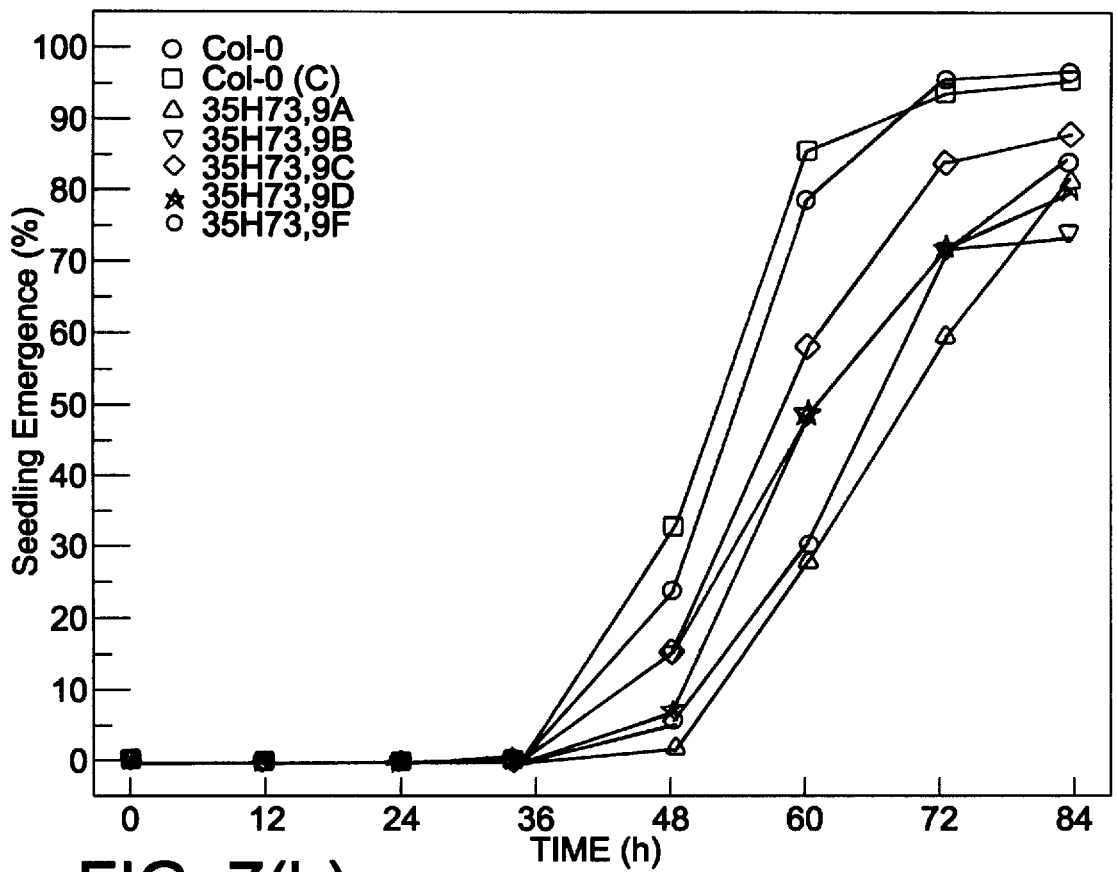
FIG. 7B is a graph showing the effect of ACOX antisense on seedling emergence.

FIG. 7A & 7B: Dependence of early post-germinative growth of ACOX antisense seedlings on exogenous carbohydrate.

Figure 8A:
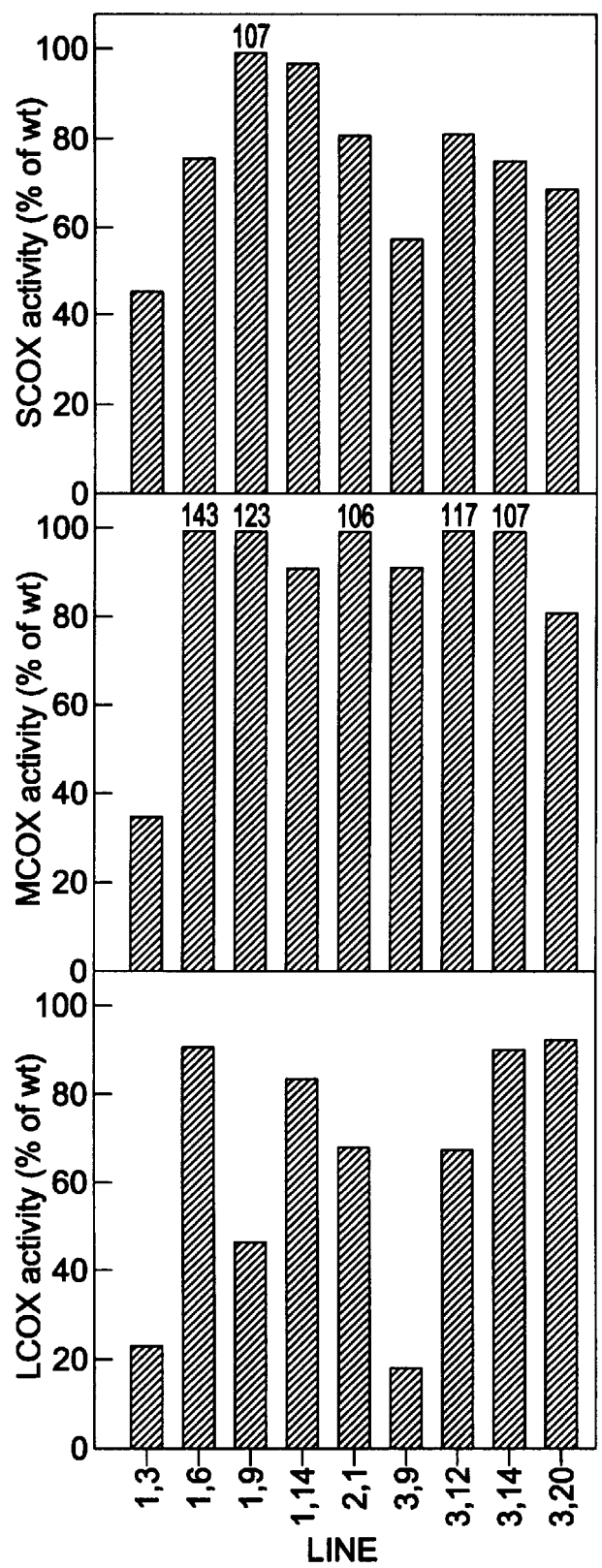
FIG. 8A shows reduced ACOX activities in antisense seedlings transformed with pJO35H.
Figure 8B:
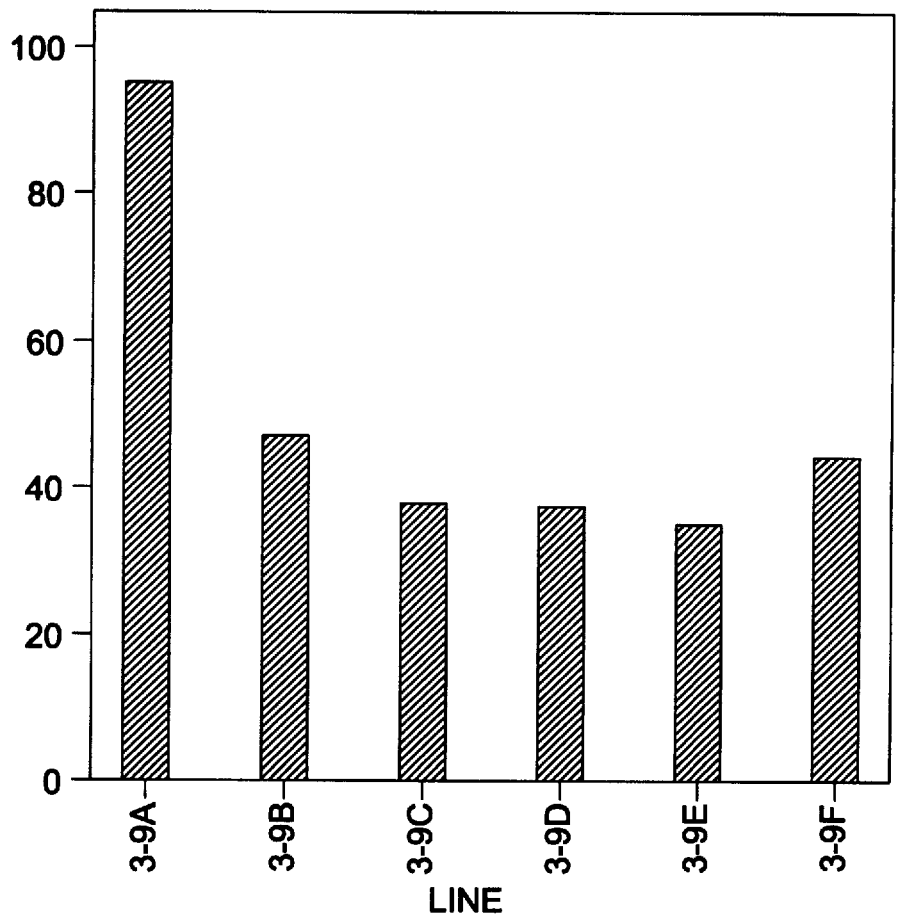
FIG. 8B shows LCOX activity in progeny of an ACOX antisense line.

FIG. 8A & 8B: Reduced ACOX activity in antisense lines.

Figure 9:
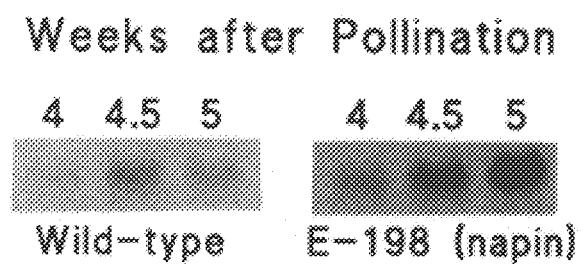
FIG. 9 shows the induction of genes of fatty acid catabolism in developing seeds of plants (*Brassica napus*) genetically engineered to produce lauric acid.

FIG. 9: Induction of genes of fatty acid catabolism in developing seeds of plants genetically engineered to produce lauric acid.

EXAMPLE 1

Fatty acid Contents and ACOX Activities in Arabidopsis Mutants that Require an Exogenous Carbohydrate Source for Germination and Growth A number of EMS mutagenised seed lines accumulate various different non-polar lipids that are not present in wild type plants. Arabidopsis seedlings requiring an exogenous carbohydrate supply for growth were selected from a population of M2seed ultimately derived from ethylmethylenesulfonic acid (EMS) mutagenized Col-0 seed. The general procedures for mutagenizing seed the EMS and selecting for mutants are described in detail in *Arabidopsis* (Meyerowitz & Somerville, eds., Cold Spring Harbor Laboratory Press, 1994). The phenotype of these mutants is a drastically reduced growth compared to wild-type Col-0 when grown on agar plates containing ½ MS salts, but no carbohydrate. The growth of mutant seedlings in the presence of exogenous carbohydrate is similar to that of wild-type Col-0.

All seeds were germinated in petri dishes on a 25 ml, 0.8% agar base containing ½ concentration of Murashige and Skoog salts (½ MS salts) [Murashige and Skoog (1962) *Physiol. Plant* 15, 473], 1x Gambourg's B5 vitamins, and with or without sucrose. All seeds were surface sterilized by soaking for 8 minutes in a solution of 50% sodium hypochlorite containing 0.05% Triton X-100 and left in $H_2O$ at 4° C. for at least 24 hours before being plated under sterile conditions in a flow hood.

Lipid contents of mutant seeds, both endogenous and in storage lipids, were determined by thin-layer chromatography of lipid extracts isolated according to standard protocols [Kates (1986) *Techniques of lipidology: Isolation, Analysis, and Identification of Lipids,* 2nd ed. Elsevier Press, Amsterdam]. In each case the lipids from 5 seeds or 5-day old plantlets from 5 seeds were extracted, resuspended each in the same volume of chloroform and chromatographed on silica gel plates using hexane/ether/acetic acid (90:10:1) as the running solvent. The lipids were visualized by spraying the plates with concentrated $H_2SO_4$ and heating them at 160° C. for a few minutes. An example of a mutant containing a new lipid in seeds and one exhibiting the accumulation of an aliphatic compound during post-germinative growth are shown in FIG. 2A.

Mutants exhibiting the sucrose-dependent-growth phenotype due to disrupted β-oxidation would also be expected to exhibit reduced ACOX activity, either due to a mutation in an ACOX gene or because ACOX activity is directly tied to the flux through β-oxidation (Chu et al. (1994) *Biochem. J.* 302, 23]. Therefore, groups of 100 4-day old mutant seedlings were analyzed for ACOX activity as specified in Example 2. The mutants analyzed exhibited reduced ACOX activity with $C_{10}$CoA (MCOX) to a certain degree (FIG. 2B).

EXAMPLE 2

Identification of Three Acyl-CoA Oxidases in the Brassicaceae Species *Arabidopsis Thaliana*

Previous work by one of the authors has shown that three acyl-CoA oxidases exist in the monocotyledonous species *Zea Mays*. The basis for their identification was the different relative levels of ACOX activity, determined with a short- ($C_6$-CoA), a medium- ($C_{10}$-CoA), and a long-chain ($C_{16}$-CoA) acyl-CoA), a that existed in maize tissues of various development and metabolic states [Hooks et al. (1994) *Plant Physiol.* 105, s710; Hooks et al. (1995) *Phytochemistry* 40, 657]. A similar analysis of ACOX activity in Arabidopsis during post-germinative growth on senescence, using the acyl-CoA substrates preferred by each maize enzyme, has shown the three corresponding ACOXs, LCOX, MCOX, and SCOX to exist in the dicotyledonous species, *Arabidopsis thaliana*. All protein extraction and ACOX activities measurements were done according to the method of Hooks et al (1995) *Phytochemistry* 40, 657.

For the analysis of ACOX activity in Arabidopsis seedlings, Col-0 seeds were germinated on agar plates containing ½ MS salts and 20 mM sucrose. Each day for eight days 100 seedlings were taken, the fresh tissue weight recorded, and then each group of 100 seedlings was extracted and assayed for ACOX activity with the three substrates. Different relative levels of ACOX activity with the three different substrates is apparent (FIG. 3A).

For the analysis of ACOX activity in senescing leaves of Arabidopsis, leaves from mature Col-0 plants were excised and incubated in the dark for one to 10 days on moist filter paper. Proteins were extracted from the leaves and ACOX activities measured with the three substrates. A different time course of induction and diminution of ACOX activity with each of the three substrates is again apparent (FIG. 3B). The profiles of ACOX activity were compared to the glyoxylate cycle enzyme isocitrate lyase (ICL), an enzyme known to be induced during the senescence of leaves. ICL activity is generally regarded as an indicator of high degrees of fatty acid catabolism.

EXAMPLE 3

Identification of cDNA Sequences Coding for Enzymes of β-oxidation

All cDNA clones were obtained from the Arabidopsis Biological Resource Center, DNA Stock Center (1060 Carmack Rd. Columbus, Ohio 43210-1002). The cDNA clones for the acyl-CoA oxidases (SEQ ID NO 1 & SEQ ID NO 2), and 3-ketoacyl-CoA thiolase (SEQ ID NO:3) were provided as *E. coli* bacterial colonies containing the cloning vector λ-Ziplox (GIBCO BRL) into which each cDNA clone was directionally inserted 5' to 3'. The cDNA clone for the multifunction protein, FAFJ01, was provided as an *E. coli* bacterial colony containing the clone directionally inserted 5' to 3' into λ-ZAP II (Stratagene) (SEQ ID NO:4). The sequences for each clone, determined by partial sequencing of the 5' end [Newman, et al., (1994) Plant Physiol. 106, 1241–1255], are given below. Each cDNA clone was identified by sequence comparison to known β-oxidation enzymes using the tBlastn program available by electronic mail at blast@ncbi.nlm.nih.gov, and scored with the default values of the algorithm. The score indices given below for each cDNA are generally regarded as proof of their identification [Altschul et al. (1990) J. Mol. Biol. 215, 403]. The sequence of each cDNA clone provided was confirmed by us using standard sequencing techniques.

---

Acyl-CoA Oxidases:
DEFINITION 519 Arabidopsis thaliana cDNA clone 35H7T7.
ACCESSION T04472 (SEQ ID NO:1)

| | | | | | |
|---|---|---|---|---|---|
| 1 | ATTGAGACAC | AGGTGATTGA | TTATAAAACT | CAGCAGAACA | GGCTATTTCC |
| 51 | TCTGCTAGCA | TCTGCATATG | CATTTCGATT | TGTTGGAGAG | TGGCTAAAAT |
| 101 | GGCTGTACAC | GGATGTAACT | GAAAGACTGG | CGGCTAGTGA | TTTCGCAACT |
| 151 | TTGCCTGAGG | CTCATGCATG | CACTGCAGGA | TTGAAGTCTC | TCACCACCAC |
| 201 | AGCCACTGCG | GATGGCATTG | AAGAATGTCG | TAAGTTATGT | GGTGGACATG |
| 251 | GATACTTGTG | GTGCAGTGGG | CTCCCCGAGC | TGTTTGCTGT | ATATGTTCCT |
| 301 | GCCTGCACAT | ACGAAGGAGA | CAATGTTGTG | CTGCAATTAC | AGGTTGCTCG |
| 351 | ATTCCTCATG | AAGACAGTCG | CCCAGCTGGG | ATCTNGAAAG | GTTCNGTTTG | wherein N = A, C, G or T
DEFINITION 858 Arabidopsis thaliana cDNA clone 5F12T7P.
ACCESSION T04810 (SEQ ID NO:2)

| | | | | | |
|---|---|---|---|---|---|
| 1 | GTGCGTTGAG | ATTCCGTTCT | GTGAGAATAC | CCCGTGATAA | TCTTCTCAAT |
| 51 | CGTTTTGGAG | ATGTGTCCCG | AGATGGGACG | TATACAAGTA | GTTTGCCAAC |
| 101 | AATCAATAAA | AGATTTGGTG | CAACACTCGC | TGAGCTTGTA | GGTGGTCGAG |

-continued

| 151 | TTGGCCTTGC | CTATGCATCT | GTTGGCGTCC | TTAAAATCTC | TGCAACGATT |
| 201 | GCCATTCGTT | ATTCTCTTCT | AAGACAACAA | TTCGGGCCTC | CAAAGCAACC |
| 251 | TGAGGTCAGT | ATTCTCGATT | ACCAGTCTCA | ACAACACAAG | CTCATGCCGA |
| 301 | TGTTAGCCTC | CACCTATGCA | TACCATTTTG | CAACTGTATA | CCTTGTGGGG |
| 351 | GAATATTCAG | AGATGAAGAA | GGCTCACGGT | GAGCAATTGG | TTGCTGATGT |
| 401 | CCATGCACTC | TCTGCTGGGC | TCAAATCTTT | GTACGGGTTT | CACGCAGGGT |
| 451 | CTCGCCTTAG | AAAGCTTTTG | | | |

TBlastN of dBest
Query = Rat ACOX j02752 (661 letters)

|  | reading Frame | High Score | Probab. P(N) N |
| --- | --- | --- | --- |
| Sequence producing High-scoring Segment Pairs: 35H7T7 | | | |
| gnl/dbest/21287 T04472 cDNA Lambda-PRL2 A. thaliana 5F12T7P | H ... +1 | 380 | 5.2e-45 1 |
| gnl/dbest/2162S T04810 cDNA Lambda-PRL2 A. thaliana Multifunctional Protein: | H ... +3 | 120 | 1.5e-20 3 |

DEFINITION    A. thaliana transcribed sequence; clone FAFJ01
ACCESSION    Z31666 (SEQ ID NO:3)

| 1 | CCTGGTGGGA | AGCCTATATC | AGTACCTGAT | AAAGAAATTG | TAGAGATGAT |
| 51 | CTTATTCCCT | GTTGTCAACG | AGGCATGCCG | CGTCCTAGAT | GAAGGAGTTG |
| 101 | TGATCCGAGC | CTCAGACTTG | GACATTGCGT | CTGTCCTTGG | AATGAGTTTT |
| 151 | CCTTCTTACC | GGGGAGGAAT | TGTTTTCTGG | GCAGACACTG | TTGGCCCAAA |
| 201 | GTACATATAT | GAGAGGCTCA | AGAAATTGTC | GGAGACTTAT | GGCAGCTTTT |
| 251 | TCAMACCATC | GAGGTATCTG | GAGGAAAGAG | CAATGCAATG | GAATGCTTTT |
| 301 | TGAGTGAATC | GAAATCGTCG | AGGTCCACAT | TGTGACGGCG | TTTCA | wherein M = A or C.
TBlastN of dBest
Query = Cucumber MFPx78996 (725 letters)

|  | reading Frame | High Score | Probab. P(N) N |
| --- | --- | --- | --- |
| Sequences producing High-scoring Segment Pairs: | | | |
| gnl/dbest/44380 Z31666 cDNA Strasbourg-A A. thaliana 3-ketoacyl-CoA thiolase (thiolase): | ... +1 | 328 | 8.1e-38 1 |

DEFINITION    442 Arabidopsis thaliana cDNA clone 39H3T7.
ACCESSION    T04395 (SEQ ID NO:4)

| 1 | AACAGATCCG | AATTTTATCT | TTAATCAGCC | GGAAAAAATG | GAGAAAGCGA |
| 51 | TCGAGAGACA | ACGNGTTCTT | CTTGAGCATC | TCCGACCTTC | TTCTTCTTCT |
| 101 | TCGCACAATT | ACGAGGCTTC | TCTATCTGCT | TCTGCTTGCT | TGGCTGGGGA |
| 151 | CAGTGCTGCA | TATCAGAGGA | CCTCTCTCTA | TGGAGATGAT | GTTGTCATTG |
| 201 | TCGCGGCACA | TAGGNCTCCA | CTATGCAAGT | CCAAACGTGG | CAATTTCAAG |
| 251 | GGTACATATC | CCGCTGATTT | GCTCGCACCT | NTTTTGAGGG | CATTGATAGA |
| 301 | GAAGACGCAT | CTAAACCCCC | NGTGAAGTAG | GTGACATTTT | TGTGGGNACT |
| 351 | CTTTTTGCAC | CNCGNTCTTA | GAGAGGCCAC | TTGANTTCAG | GNATGGCTGC | wherein N = A, C, G or T.
TBLASTIN of dBest
Query = Cucumber Thiolase 67696 (462 letters)

|  | reading Frame | High Score | Probab. P (N) N |
| --- | --- | --- | --- |
| Sequence producing High-scoring Segment Pairs: | | | |
| gnl/dbest/21210 T04395 cDNA Lambda-PRL2 A. thaliana | H ... +2 | 291 | 7.1e-38 2 |

EXAMPLE 4

Construction of Antisense vectors, pJO5F, pJO35H, pJO39H, and pJOFAF

Liquid E. Coli were grown in standard LB media containing the appropriate antibiotics at 200 RPM on rotary shakers at 37° C. and E. coli colonies were grown on standard LB-agar plates in an incubator at 37° C. [*Protocol and Applications Guide,* 2nd ed. Promega]. Liquid agrobacterium cultures were grown in standard LB media containing the appropriate antibiotics at 220 RPM on rotary shakers at 28° C. and Agrobacterium colonies were grown on standard LE plates containing the appropriate antibiotics in an incubator at 28° C.

For all manipulations requiring DNA amplification in *E. coli,* either strain DH5oc (suppE44, ΔlacU169 [φ80lacZΔM15], hsdR17, recA1. recA1, endA1, gyrA96, thi-1, relA1) or XL1-Blue (suppE44, hsdR17, recA1, endA1, gyrA96, thi-1, relA1, lac, F' [proAB$^+$, lacI', lacZΔM15, Tn10 (tet)]) were used as recipients of recombinant plasmids. Plant transformation using the binary vector system was conducted using *Agrobacterium tumefaciens* strain GV3101 containing a vir$^+$ Ti-plasmid lacking the t-DNA region.

The cloning of cDNA fragments into pJO530 (pBIN19 derivative [Bevan et al. (1984) Nuc. Acids Res. 12, 8711]) and the subsequent transformation of E. coli and Agrobacterium were performed according to standard procedures [Sambrook et al., (1989) *Molecular Cloning: A Laboratory Manual,* 2nd ed.]. cDNA fragments in λ-Ziplox were excised by restriction digest of the plasmid with XbaI and Sal I. The fragments were gel-purified, removed from the agarose (GeneClean™, BIO 101 Inc. La Jolla, Calif.), and ligated into pJO530, which was previously linearized by restriction digest with xBA I and Sal I. FIG. 4A shows generic maps for vectors pJO5F, pJO35H, and pJO39H where the cDNA fragment was originally cloned into λ-Ziplox. The cDNA fragment in λ-ZAP II was excised by restriction digest of the plasmid with Kpn I and XbaI. The fragment was gel-purified, removed from the agarose, and ligated into pJO530, which had been linearized by restriction with Kpn I and Xba I. FIG. 4B shows the plasmid map of vector pJOFAF. For all vectors proper insertion of cDNA fragments in the antisense orientation was determined by restriction digest analysis and sequencing of the insert. Sequencing of cDNA inserts in pJO530 was conducted in both directions using primers specific to regions flanking the multiple cloning site-pJO530-5', 5'-TGAACTCTATCATTGATAG-3'; pJO530-3', 5'-AGTAACGGGTGATATATTCA-3'.

EXAMPLE 5

Construction of "Double" Antisense Vector, pJO530

The construct, pJO530 (FIG. 5) was made by inserting cDNA 5F into pJO35H. The cDNA fragment 5F was prepared as described in Example 4 and blunt-ended by filling the recessed termini using Klenow. The vector pJO35H was prepared by restriction digest with Sma I and the ends dephosphorylated with calf-intestinal alkaline phosphatase. After repurification of the cDNA and linearized vector, cDNA 5F was ligated into pJO35H and an aliquot used to transform E. coli XL1-blue cells. Plasmid DNA was isolated from selected transformants showing resistance to kanamycin and checked for the presence of both inserts using a combination of double and triple restriction digests using Kpn I, Xba I, and Sal I. The proper orientation of 5F was determined by sequencing using primer pJO5305'.

EXAMPLE 6

Production of Transgenic Plants

Arabidopsis plants to be used for transformation were grown in growth chambers at 20° C. under a constant illumination of 70 $\mu$EM/m$^2$ with 12 plants per 3.5" pot. Approximately 3–4 weeks after seed sowing the primary bolts of the plants were removed to facilitate growth of multiple secondary bolts. Plants were transformed by vacuum infiltration (Bechtold et al., Comptes tendus de L'Academie des Sciences Serie III Sciences de la Vie (1993) 316: p. 1194) 4 to 8 days after removal of the bolts.

Large liquid cultures of Agrobacterium to be used for transformation were prepared as specified in Example 4 above and transferred to infiltration media (½ MS salts [Murashige and Skoog (1962) Physiol. Plant. 15, 473], 1x Gambourg's B5 vitamins, 5% sucrose, and 0.044 $\mu$M benzylamino purine), by centrifigation and resuspension to an OD$_{600}$ of 0.8. Vacuum infiltration was completed by immersing the pots upside down into a beaker containing the Agrobacterium suspension, which was then placed in a vacuum dessicator. A vacuum was applied for a duration of either 2 or 5 minutes after the initial intense bubbling—of solution moving into the soil—had subsided. The pots of vacuum infiltrated plants were then returned to the growth room. Plants (T1-generation) were allowed to grow without further manipulation except for watering when necessary. Seed (T2 generation) was collected approximately 2 to 2 ½ months after vacuum infiltration.

Transformed seed were selected by vigor of growth on ½ MS-agar plates (described in Example 1) containing 30 $\mu$g/ml hygromycin. Resistant plantlets (T2 plants) were transferred to soil and allowed to grow as described for the T1 generation plants. When the plants were large enough, DNA was extracted from individual plants as subjected to Southern analysis using the cDNA as a probe [Sambrook et al., (1989) *Molecular Cloning: A Laboratory Manual,* 2nd ed] to determine if the cDNA had been incorporated into the genome and in what numbers of copies (FIG. 6). Plants, selected for their resistance to hygromycin were found to have one to multiple copies of the cDNA.

EXAMPLE 7

Dependence of ACOX Antisense Seedling Growth on Exogenous Carbohydrate

Seedlings antisense in ACOX show reduced post-germinative root growth compared to Col-0 when germinated and grown on media not supplemented with sucrose, as would be expected for those disrupted in $\beta$-oxidation. Approximately 50 T3-generation seed from various antisense lines produced form constructs pJO5F and pJO35H were prepared and plated (as described in Example 1) in petri dishes containing ½ MS agar-media with or without 20 mM sucrose. Five days after plating, root lengths of all seedlings were measured and averaged for each antisense line. The data was analyzed as the ratio of average root length for seedlings grown without sucrose to that of seedling supplemented with sucrose (FIG. 7A). A ratio lower than that for Col-0 indicates reduced growth. The average root length for antisense seedlings was similar to that for Col-0 in the presence of sucrose.

The trait of reduced post-germinative growth was shown to be heritable through the corresponding root growth analysis of the progeny of ACOX antisense line 35H3-9. Approximately 150 seed from the T3 generation of this antisense line—a line exhibiting drastically reduced LCOX activity (see Example 7)—were germinated and grown on ½ MS agar plates containing 20 mM sucrose and 30 $\mu$g/ml hygromycin. Thirty-three seedlings were selected and transferred to soil. Of the thirty-three seedlings, six survived to maturity and produced seed. In each case, the antisense seedlings showed a reduced capacity for growth compared to Col-0 (FIG. 7B).

EXAMPLE 8

Reduced ACOX Activity in ACOX Antisense Lines

Groups of ACOX seedlings used for ACOX activity analyses were prepared and extracted as specified in Example 2. Several lines exhibited reduced ACOX activity either in all three enzymes or in LCOX (FIG. 8A). There was a general correlation among those seedlings exhibiting reduced post-germinative growth and reduced ACOX activity. One line, that exhibiting only reduced LCOX activity, was chosen for LCOX analysis in T4 progeny (see Example 6). Seedlings from the T4 progeny also exhibited reduced LCOX activity (FIG. 8B).

EXAMPLE 9

Induction of Fatty Acid Catabolism Genes in Developing Seeds of Brassica Napus Genetically Engineered to Produce the Novel Fatty Acid Lauric Acid These plants have been genetically modified to produce lauric acid in seeds, either free or in lipids, by expressing the California Bay medium-chain acyl-carrier protein thioesterase (MCTE) under the control of the seed-specific napin promoter as described by [Voelker et al. supra] herein incorporated by reference. Plants expressing MCTE in vegetative tissues was accomplished through use of the cauliflower 35S promoter. Such plants exhibit high expression of the MCTE, but little or no accumulation of medium-chain fatty acids, especially in vegetative tissues.

These seeds for the laurate-producing Brassica plants were obtained from Michigan State University. Dry Bassica seeds were imbibed in H$_2$O and kept at 4° C. for at least 24 hours, but not longer that 4 days. Four seeds were sown per 12" pot containing compost/vermiculite (2:1). Plants were grown at 20° C. under constant illumination of 70 $\mu$E/m$^2$, well watered, and given fertilizer supplements weekly. The first flowers appeared approximately 6 weeks after sowing.

Flowers were self-pollinated by hand and affixed with a label specifying the date in order to normalize morphological staging of the developing seed. At the specified times seeds were harvested from the maturing pods. RNA extraction and Northern blot analysis ICL expression, a gene market for fatty acid catabolism, were conducted according to standard procedures. A significant induction of expression of the ICL gene was observed in the transgenic seeds compared to those from non-genetically modified Brassica plants (FIG. 9). This demonstrated that the excess production of fatty acids leads to an increase in the machinery responsible for their catabolism.

We claim:

1. A nucleotide sequence comprising a DNA sequence encoding an antisense RNA molecule operably linked to a promoter and a terminator, said promoter and terminator functioning in a plant cell, wherein said antisense RNA molecule is complementary to a portion of the coding sequence for a protein having enzymatic activity in the peroxisomal β-oxidation of fatty acids in plant cells wherein said protein is selected from the group consisting of an acyl-CoA oxidase, multifunctional protein and 3-ketoacyl CoA thiolase.

2. A nucleotide sequence according to claim 1 wherein the antisense RNA molecule is complementary to a sense mRNA molecule encoding for a protein selected from the group acyl-CoA oxidases, multifunctional protein and 3-ketoacyl-CoA thiolase or fragments thereof.

3. A nucleotide sequence according to claim 1 wherein the promoter is selected from the group consisting of constitutive, inducible and developmentally regulated promoters.

4. The nucleotide sequence of claim 1, wherein said nucleotide sequence further comprises a DNA sequence encoding a market protein, said market protein operably linked to a promoter and a terminator, said promoter and terminator functioning in a plant cell.

5. A nucleotide sequence comprising a transcriptional regulatory sequence operably linked to at least two DNA sequences, each DNA sequence encoding an antisense RNA molecule wherein said antisense RNA molecule is complementary to a portion of the coding sequence for a protein having enzymatic activity in the peroxisomal β-oxidation of fatty acids in plant cells wherein said protein is selected from the group consisting of an acyl-CoA oxidase, multifunctional protein and 3-ketoacyl CoA thiolase.

6. The nucleotide sequence of claim 5, further comprising a DNA sequence encoding a marker protein, said marker protein operably linked to a promoter and a terminator, said promoter and terminator functioning in a plant cell.

7. A plasmid comprising the sequence of claim 1 or 5.

8. A bacterium comprising the plasmid of claim 7.

9. A plant cell having integrated into its genome the nucleotide sequence of claim 1 or claim 5.

10. A plant having integrated into its genome the nucleotide sequence of claim 1 or claim 5.

11. Seed of the plant of claim 10.

12. Progeny of the plant of claim 10.

13. A plant expressing in its cells an antisense RNA that is complementary to a portion of the coding sequence for a protein having enzymatic activity in the peroxisomal β-oxidation of fatty acids in plant cells wherein said protein is selected from the group consisting of an acyl-CoA oxidase, multifunctional protein and 3-ketoacyl CoA thiolase.

* * * * *